US008057635B2

(12) United States Patent
Foody, Sr.

(10) Patent No.: US 8,057,635 B2
(45) Date of Patent: Nov. 15, 2011

(54) METHOD AND SYSTEM FOR THE LARGE SCALE COLLECTION, PREPARATION, HANDLING AND REFINING OF LIGNO-CELLULOSIC BIOMASS

(75) Inventor: Patrick Foody, Sr., Hudson (CA)

(73) Assignee: Iogen Energy Corporation, Ontario (CA)

( * ) Notice: Subject to any disclaimer, the term of this patent is extended or adjusted under 35 U.S.C. 154(b) by 414 days.

(21) Appl. No.: 11/769,850

(22) Filed: Jun. 28, 2007

(65) Prior Publication Data
US 2008/0038815 A1    Feb. 14, 2008

Related U.S. Application Data

(60) Provisional application No. 60/836,737, filed on Aug. 10, 2006.

(51) Int. Cl.
*D21C 5/02* (2006.01)

(52) U.S. Cl. ............ 162/41; 162/42; 162/43; 162/91; 162/92; 162/93; 162/94; 162/95; 162/96; 162/97; 162/98; 162/99; 162/23; 162/24; 162/26; 162/28

(58) Field of Classification Search .......... 162/41–43, 162/91–99, 23, 24, 26, 28
See application file for complete search history.

(56) References Cited

U.S. PATENT DOCUMENTS

| | | | |
|---|---|---|---|
| 4,305,688 A | 12/1981 | Savins | 406/197 |
| 4,461,648 A | 7/1984 | Foody | 127/37 |
| 4,808,526 A | 2/1989 | Lawford | 435/161 |
| 5,755,928 A | 5/1998 | Foody et al. | 162/49 |
| 5,916,780 A | 6/1999 | Foody et al. | 435/99 |
| 6,616,375 B1 * | 9/2003 | Eriksson | 405/51 |
| 6,838,000 B2 * | 1/2005 | Braun | 210/603 |
| 2004/0025715 A1 | 2/2004 | Bonde et al. | 99/485 |
| 2004/0034262 A1 * | 2/2004 | Van de Beld et al. | 585/240 |
| 2004/0168960 A1 | 9/2004 | Holtzapple et al. | 210/101 |
| 2004/0171136 A1 | 9/2004 | Holtzapple et al. | 435/283.1 |
| 2006/0048920 A1 | 3/2006 | Helleur | 165/108 |

(Continued)

FOREIGN PATENT DOCUMENTS

GB    2 145 732 A    4/1985

(Continued)

OTHER PUBLICATIONS

Amit Kumar et al, "Innovation in biomass transport. Workshop on Biomass Feedstock Integration for Bio-industry in Canada"; Feb. 4, 2005.

(Continued)

*Primary Examiner* — Jessica L Ward
*Assistant Examiner* — Erin Saad
(74) *Attorney, Agent, or Firm* — Fitzpatrick, Cella, Harper & Scinto

(57) ABSTRACT

A system for collecting ligno-cellulosic biomass over a large area to enable the commercial refining of biomass from 2,500 to in excess of 50,000 tons of biomass per day to produce ethanol or other products. The biomass is collected at a series of collection points and then transported through a network of conduit "loops" interconnecting each of the collection points and the central refining plant. The water used to transport the biomass, as a slurry, is recovered and sequentially recycled in the same pipeline system to push the biomass slurry around the system in a "loop".

10 Claims, 6 Drawing Sheets

U.S. PATENT DOCUMENTS

2006/0112638 A1 6/2006 Suyama et al. ............. 48/197 R
2006/0154352 A1 7/2006 Foody et al. ................. 435/161

FOREIGN PATENT DOCUMENTS

| JP | 2002-330644 A | 11/2002 |
| JP | 2005-118011 A1 | 5/2005 |

OTHER PUBLICATIONS

Amit Kumar et al, "Pipelines: Moving Biomass and Energy";Second National Conference of BIOCAP Canada, Oct. 31, 2006.

Amit Kumar et al, "Pipeline transport and simultaneous saccharification of corn stover"; Bioresource Technology 96 (2005) pp. 819-829.

* cited by examiner

TYPICAL LOOP SYSTEM

FEEDSTOCK TRANSPORT SYSTEM

SOLIDS-LIQUID SEPARATION

TYPICAL FEEDSTOCK PUMP STATION

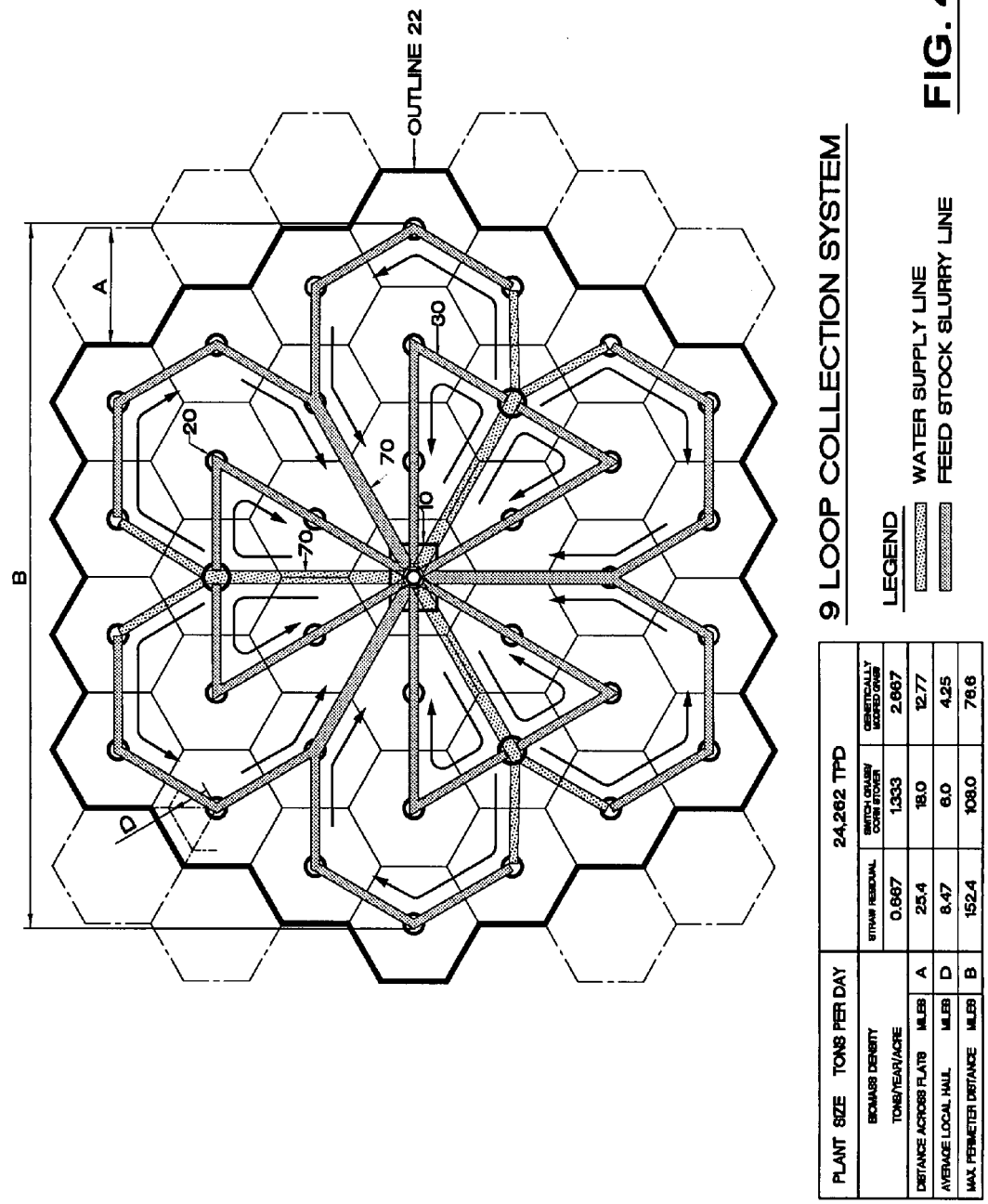

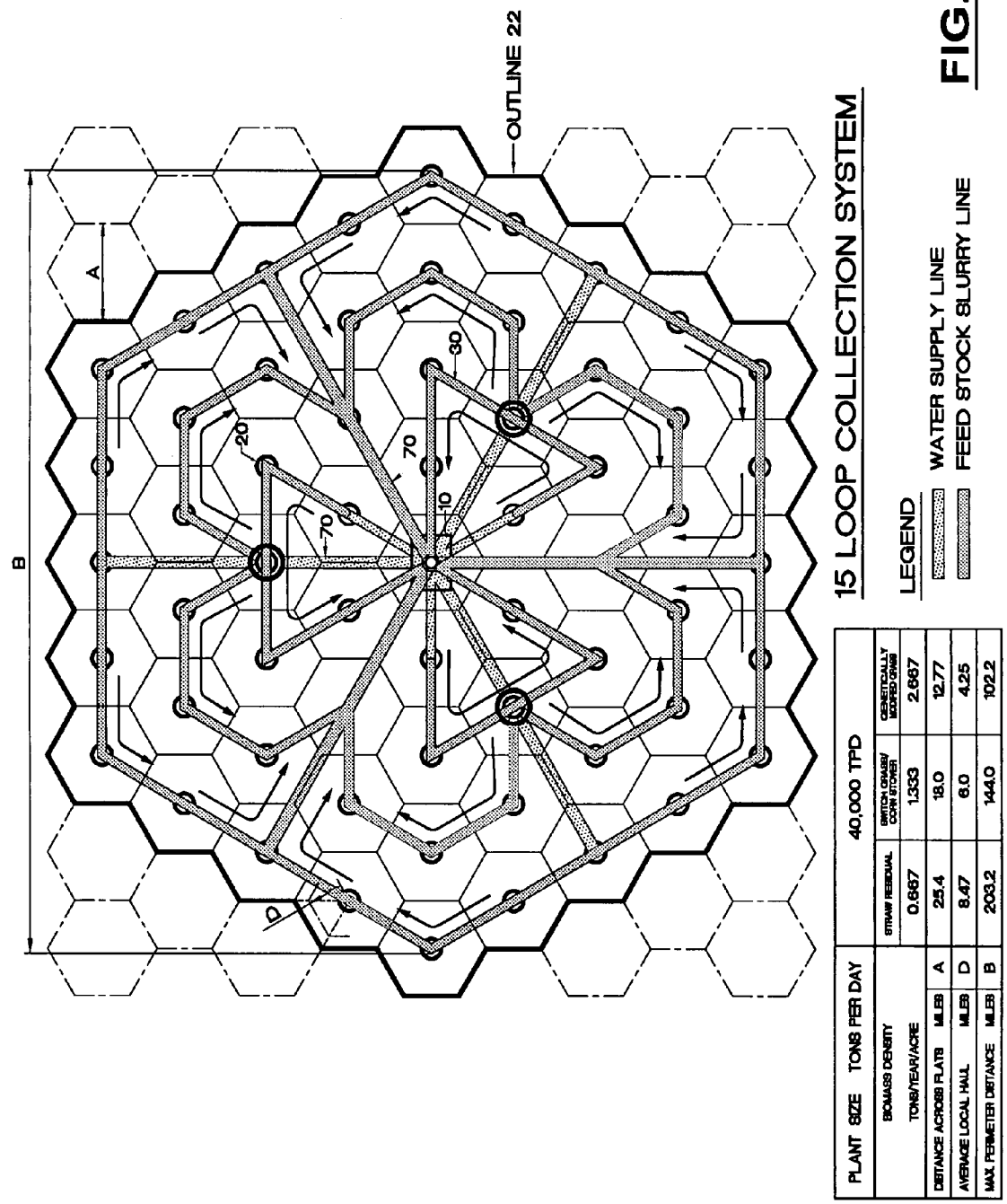

METHOD AND SYSTEM FOR THE LARGE SCALE COLLECTION, PREPARATION, HANDLING AND REFINING OF LIGNO-CELLULOSIC BIOMASS

This application claims the benefit of U.S. Provisional Application No. 60/836,737, filed Aug. 10, 2006, which is incorporated by reference.

BACKGROUND OF THE INVENTION

1. Field of the Invention

The invention is in the field of biomass collection and preconditioning for subsequent refining into ethanol and other products. Specifically, the invention is directed to the collection of biomass over a large area so as to take advantage of economies of scale. According to embodiments, the biomass may be preconditioned to a selected pH, either in stockpiles, or at a centrally located plant prior to downstream processing.

2. Description of the Related Art

U.S. Pat. No. 4,461,648 to Patrick Foody, herein incorporated by reference in its entirety, discloses technology in which cellulose is made accessible for chemical reaction by a process of steam explosion and chemical disintegration to break down the bonds between the lignin and cellulose in the biomass. During the 1970's, after the first "oil shock" occurred, the inventor was conducting research on making low-grade fiber and wood digestible to ruminant animals. He recognized that accessibility of these materials to ruminant animal microflora and accessibility to enzymes was in fact a very similar problem. Trials were conducted using steam explosion to fractionate the fiber. As it turned out, it was a much more difficult problem than simply "exploding" the fiber to fractionate the internal bonds, and involved a very narrow window across the time/temperature range at which the process could be optimized. Nevertheless, the result of these efforts, disclosed and claimed in U.S. Pat. No. 4,461,648 was a process that made the cellulose completely accessible to enzymes. This was the first breakthrough in the technology and arguably laid the foundation for biomass refining, as the science is currently called.

However, one key barrier still remains to achieving real economic competitiveness, that is, the problem of "scale." The present invention, the inventor believes, will be the last piece in the puzzle that will make biomass ethanol competitive with oil.

U.S. Pat. No. 5,916,780, to Brian Foody, et al., herein incorporated by reference in its entirety, discloses technology for pre-treating and transporting biomass, especially as it relates to the production of ethanol.

Japanese Patent No. JP2002330644 proposes a system for biomass collection. However this patent discloses a pneumatic system and does not adequately address the implementation of a large scale biomass collection and refining system.

Pipeline systems for moving woodchips are not uncommon, but these are normally used on a point-to-point basis. Peter C. Flynn, et al., *Bioresource Technology*, 96 (2005) 819-829 postulates a biomass refining system wherein the water may be pumped back either completely or in part to the beginning of the system. This requires two pipelines, as noted by the author, and is not economically viable.

In order to be viable, ethanol from biomass (also referred to herein as cellulosic ethanol) must overcome advantages that accrue to its industrial competitors, the grain ethanol and petroleum industries. One of these advantages is that the road, rail, pipeline and river infrastructure for transporting conventional energy products is already in place.

Biomass by its nature is at a significant cost and handling disadvantage as compared to these competitors. For example, grain, which is free flowing, weighs 40 lbs to 50 lbs per cubic foot, while biomass weighs 10 lbs per cubic foot in bales, and 5 lbs per cubic foot loose. The largest grain ethanol plants being currently built, without access to water or rail transportation, handle on the order of 2,500 tons per day. At a "test weight" of 5 lbs per cubic foot, the viability of a biomass refining system is largely dictated by access to road systems. The differential in the volume to be moved could challenge the capacity of most road systems. In order to take advantage of the cheaper unit cost of biomass, it is estimated that a system capable of processing significantly in excess of 2,500 tons per day of biomass would be necessary for cellulosic ethanol to compete with easily refined starch based grain ethanol.

The oil industry, the other conventional competitor to biomass refining, has the advantage of "scale" and well established pipeline systems so that it can tolerate significantly higher raw material costs.

It is estimated that a cellulosic ethanol system capable of processing in excess of 10,000 tons per day of biomass would be required to compete with oil.

Further technological and scientific advances in materials handling and physical layouts are necessary to make ethanol from biomass commercially competitive with oil, especially with regard to the economies of scale.

An important object of this invention is to overcome the difficulties and expenses that arise in connection with handling large amounts of relatively light non-free flowing biomass. The inventor herein has developed a continuous "loop" system for moving a biomass slurry along the same pipeline as the transportation water, as well as adding new biomass at more than one selected point along the pipeline. According to embodiments of the present invention, conventional delivery systems, except for local pick-ups, can be avoided altogether, in favor of the centralized and integrated network of loops described herein.

SUMMARY OF THE INVENTION

A biomass collection and refining system according to the invention comprises a biomass refining plant, a plurality of collection points and at least one conduit loop connecting the collection points and the refining plant through a continuous circulating arrangement, so that a slurry of water and biomass is transported from the collection points to the refining plant and the transportation water is recovered and reintroduced along with recovered process water to the same conduit. "Conduit," as used herein includes, without limitation, pipes, canals, or like structures. Optionally, the system comprises a plurality of loops connecting the collection points and the refining plant.

The method according to the invention involves collecting biomass at a plurality of pick-up points (also referred to herein as "collection points"). The biomass may arrive chopped, or some pH conditioning may be done at the collection points (or elsewhere along the transport path) for introduction into the cooking phase, as desired. The biomass is introduced into the conduit loop to form a slurry of biomass and liquid (such as, without limitation, a 5 wt % solids mix in water) at one or more of the collection points and is transported through at least one conduit loop connecting each of the collection points on a particular "loop" with the central refining plant where the biomass is subjected to cooking.

Water is removed from the slurry at the refining plant, using a separating device, cane press, screw press, screens or the like apparatus, and reused for continual transport of biomass through one or more conduit loops.

BRIEF DESCRIPTION OF THE FIGURES

FIG. 4 shows the expansion of the system to nine connecting loops.

FIG. 5 shows the further expansion of the system to fifteen loops with the integration of the pipelines into trunk lines for entering and leaving the plant.

DETAILED DESCRIPTION OF THE PREFERRED EMBODIMENTS

Biomass is grown crop fiber consisting primarily of cellulose, hemicellulose and lignin, and includes, without limitation, grass, switchgrass, straw, corn stover, cane residuals, general cereal wastes, wood chips and the like, that can be converted to ethanol (or other products) according to the aforesaid U.S. Pat. No. 4,461,648 and U.S. Pat. No. 5,916,780, or other known technology. Thus, as used herein, biomass includes materials that are not free flowing in their native state, such as ligno-cellulosic materials. The invention is intended to be used preferably in connection with the collection and transport of non-free flowing materials (ligno-cellulosic biomass), as these materials are conventionally the most intractable from a materials handling standpoint An acre of arable land may produce as much as 18 tons of biomass per year (sugar cane), and typically 5 tons per acre of corn stover or switch grass in a temperate climate. To ensure an adequate supply, a system according to the invention is typically designed based on 0.67 tons of biomass per acre per year (cereal grain straw) or 1.34 tons of corn stover. This refers to the average amount of biomass obtainable, accounting for domestic disappearance (including the use of biomass for other purposes), alternative crops, and the like, not the maximum amount that the land will produce. Calculations based on genetically modified grass are also included in the Tables below.

As shown in FIG. 2 through FIG. 5, collection points 20 preferably are in the center, or close to the center, of an agricultural area from which biomass will be obtained. These agricultural areas are represented as hexagons in the figures, although that representation is arbitrary, and some variation in the size, shape and topography of the collection areas will be expected. A maximum collection capacity for a facility according to the invention is preferably in a range of up to 50,000 tons per day, which could possibly require a network diameter of about 230 miles, or more. The term "network," depicted for example as network diameter B in FIGS. 2-5, refers to the diameter of the region bounded by the outermost conduits, for example. The number of collection points is not critical, and varies depending on the size of the network, and may range (for example only) between 7 and 100 collection points. Outline 22 is the extent of the agricultural areas serviced by all of the collection points 20.

Figure 2:
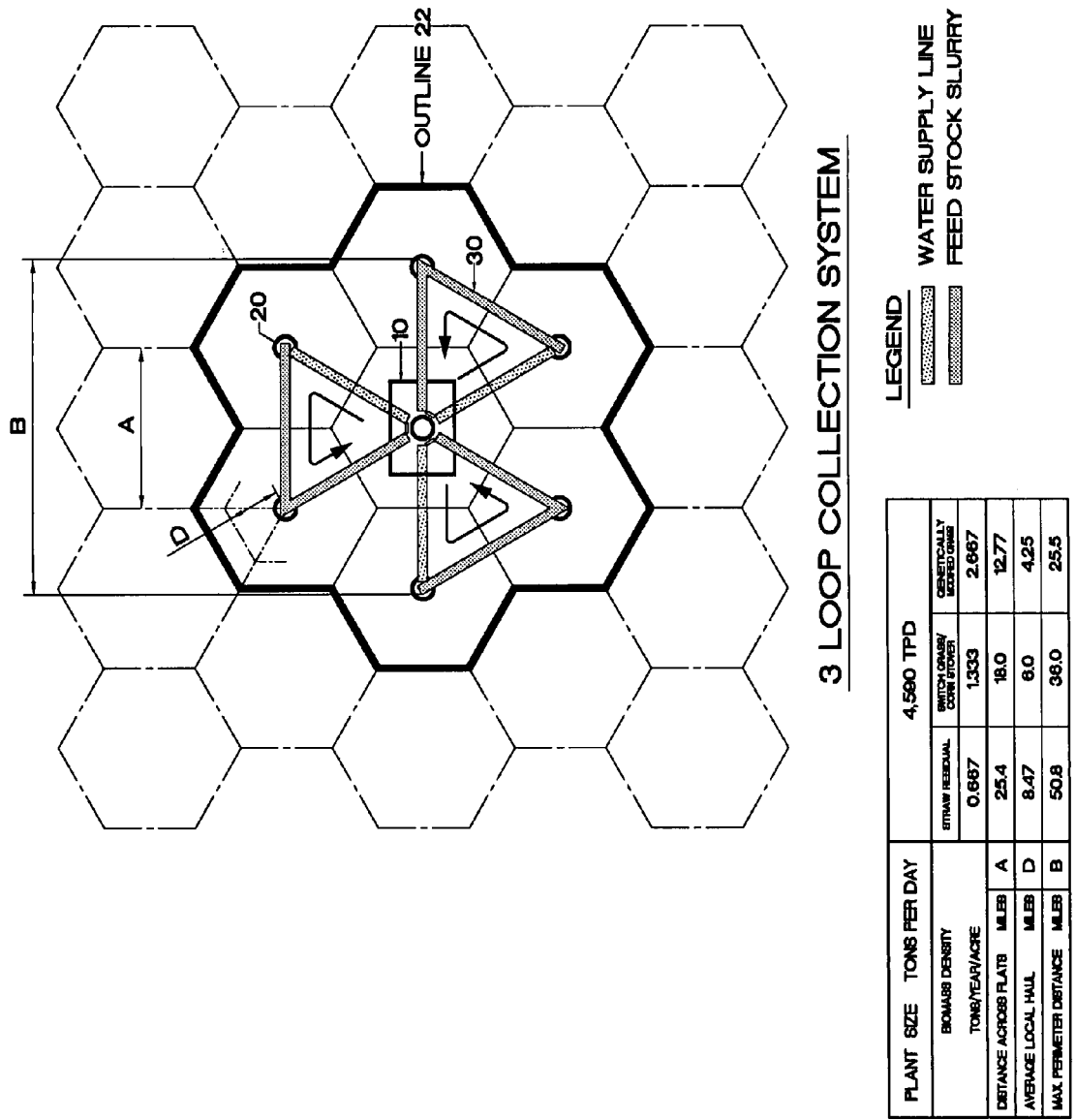
FIG. 2 depicts a typical network configuration comprising three loops entering the refining plant.

As shown in FIG. 2, the size of the total collection area is based on plant processing capability. The following projections have been made based on a plant capacity of about 5,000 tons/day, 12,500 tons/day, 25,000 tons/day, and 40,000 tons/day, resulting in a distance across the entire collection area in a range of about 50 miles to about 200 miles.

TABLE 1

(FIG. 2)

| PLANT SIZE | TONS PER DAY | | 4,590 TPD | |
|---|---|---|---|---|
| BIOMASS DENSITY TONS/YEAR/ACRE | | STRAW RESIDUAL 0.667 | SWITCH GRASS/ CORN STOVER 1.333 | GENETICALLY MODIFIED GRASS 2.667 |
| DISTANCE ACROSS FLATS MILES | A | 25.4 | 18.0 | 12.77 |
| AVERAGE LOCAL HAUL MILES | D | 8.47 | 6.0 | 4.25 |
| MAX PERIMETER DISTANCE MILES | B | 50.8 | 36.0 | 25.5 |

TABLE 2

(FIG. 3)

| PLANT SIZE | TONS PER DAY | | 12,456 TPD | |
|---|---|---|---|---|
| BIOMASS DENSITY TONS/YEAR/ACRE | | STRAW RESIDUAL 0.667 | SWITCH GRASS/ CORN STOVER 1.333 | GENETICALLY MODIFIED GRASS 2.667 |
| DISTANCE ACROSS FLATS MILES | A | 25.4 | 18.0 | 12.77 |
| AVERAGE LOCAL HAUL MILES | D | 8.47 | 6.0 | 4.25 |
| MAX PERIMETER DISTANCE MILES | B | 101.6 | 72.0 | 51.1 |

TABLE 3

(FIG. 4)

| PLANT SIZE | TONS PER DAY | | 24,262 TPD | |
|---|---|---|---|---|
| BIOMASS DENSITY TONS/YEAR/ACRE | | STRAW RESIDUAL 0.667 | SWITCH GRASS/ CORN STOVER 1.333 | GENETICALLY MODIFIED GRASS 2.667 |
| DISTANCE ACROSS FLATS MILES | A | 25.4 | 18.0 | 12.77 |
| AVERAGE LOCAL HAUL MILES | D | 8.47 | 6.0 | 4.25 |
| MAX PERIMETER DISTANCE MILES | B | 152.4 | 108.0 | 76.6 |

TABLE 4

(FIG. 5)

| PLANT SIZE | TONS PER DAY | | 40,000 TPD | |
|---|---|---|---|---|
| BIOMASS DENSITY TONS/YEAR/ACRE | | STRAW RESIDUAL 0.667 | SWITCH GRASS/ CORN STOVER 1.333 | GENETICALLY MODIFIED GRASS 2.667 |
| DISTANCE ACROSS FLATS MILES | A | 25.4 | 18.0 | 12.77 |
| AVERAGE LOCAL HAUL MILES | D | 8.47 | 6.0 | 4.25 |
| MAX PERIMETER DISTANCE MILES | B | 203.2 | 144.0 | 102.2 |

Biomass feedstocks differ in terms of how much fuel may be produced from a ton of the feedstock, and in terms of which enzymes and other techniques are used for refining the feedstock. Typically 40 to 100 gallons of fuel can be produced from a ton of biomass. It is preferable to have biomass that is approximately uniform in size collected from the different collection points according to this invention to ease the task of refining.

Figure 3:
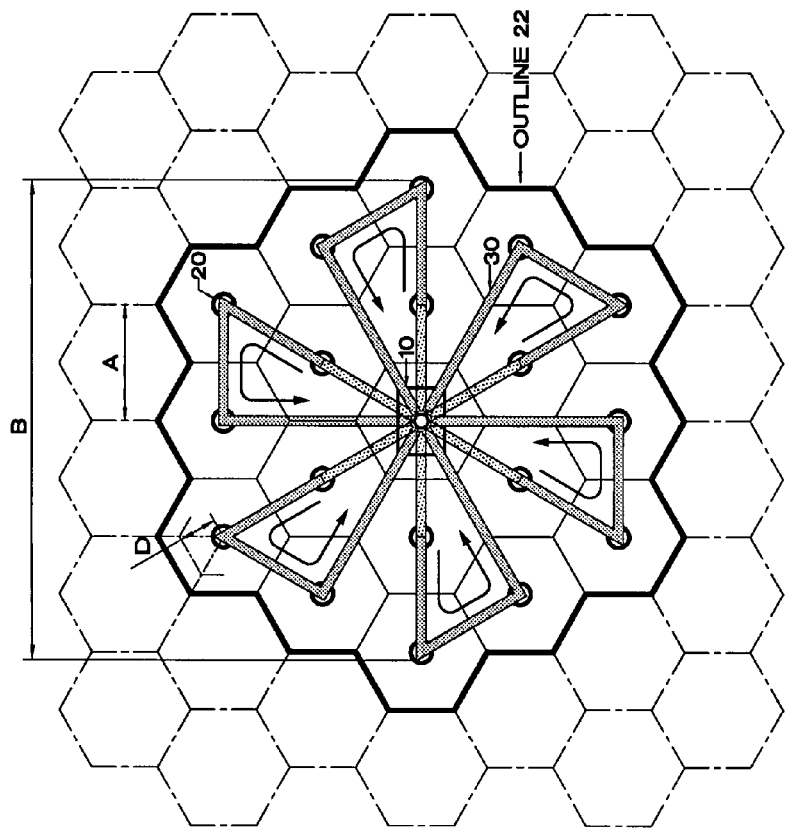
FIG. 3 depicts another configuration in which six separate loops carry material into the refining plant

A key advantage of the present invention is that the biomass is delivered to collection points by truck or farm wagons traveling a relatively short distance D to the collection points 20. For example, in a system calculated to accumulate about 12,500 tons of biomass, comprising 19 collection points, with a little over 25 miles separating the adjacent collection points (distance A), as shown in FIG. 3, and based on a collection of 0.67 tons of biomass per acre per year, the average distance D that would be traveled to a collection site would be on the order of 8.5 miles. This distance from pick-up points is suitable for local hauling, which can be done in a variety of ways by farmers. These numbers are for illustration only and are not to be considered limiting to the invention.

Figure 1:
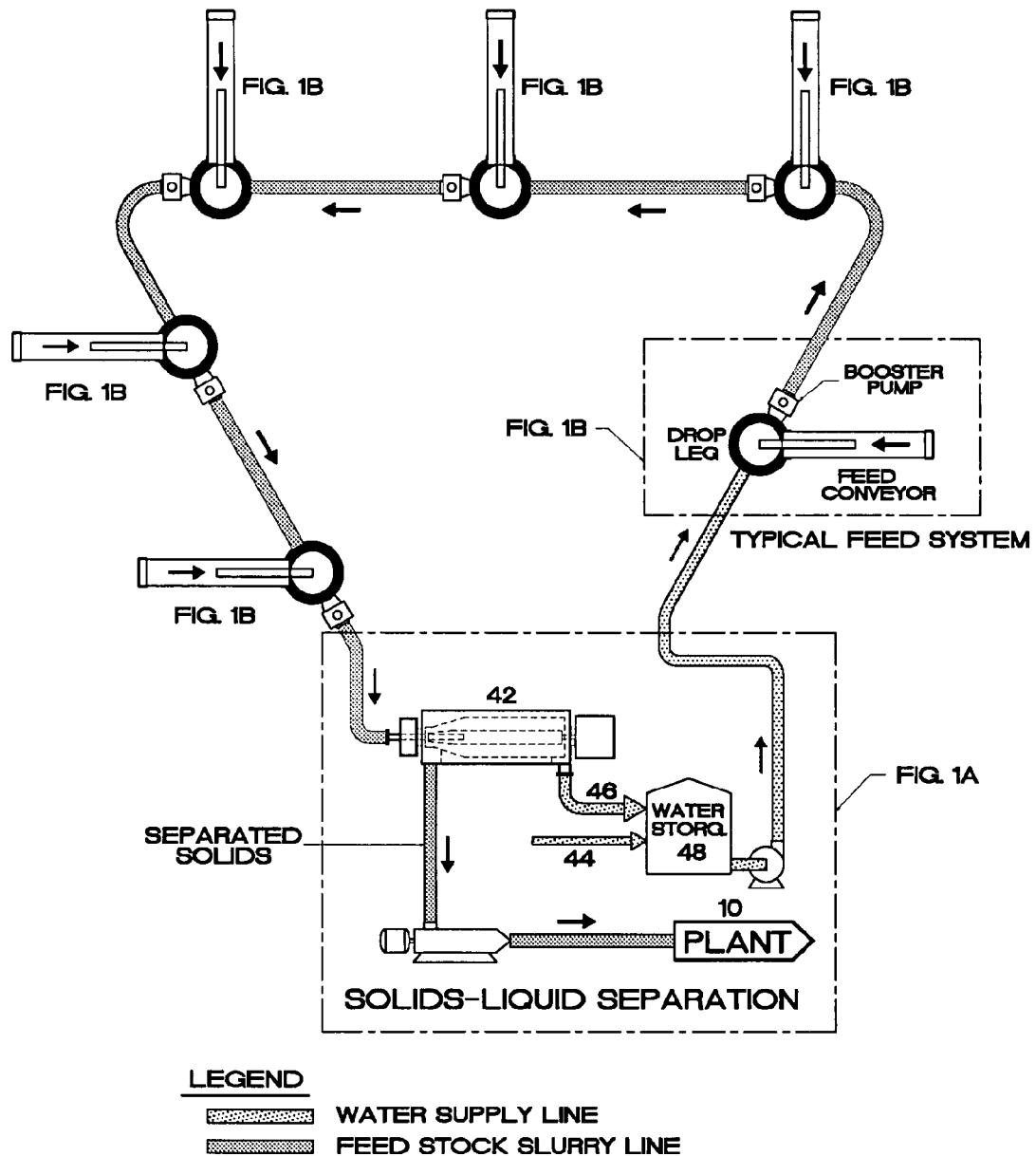
FIG. 1 depicts a single loop configuration showing the general relationship of a centrally located refining plant, a pipeline system leaving the plant, water being charged into the pipeline system, introduction of biomass at one or several points along the line, as well as the removal of the water for reuse. The biomass then goes into the refining plant.
Figure 1A:
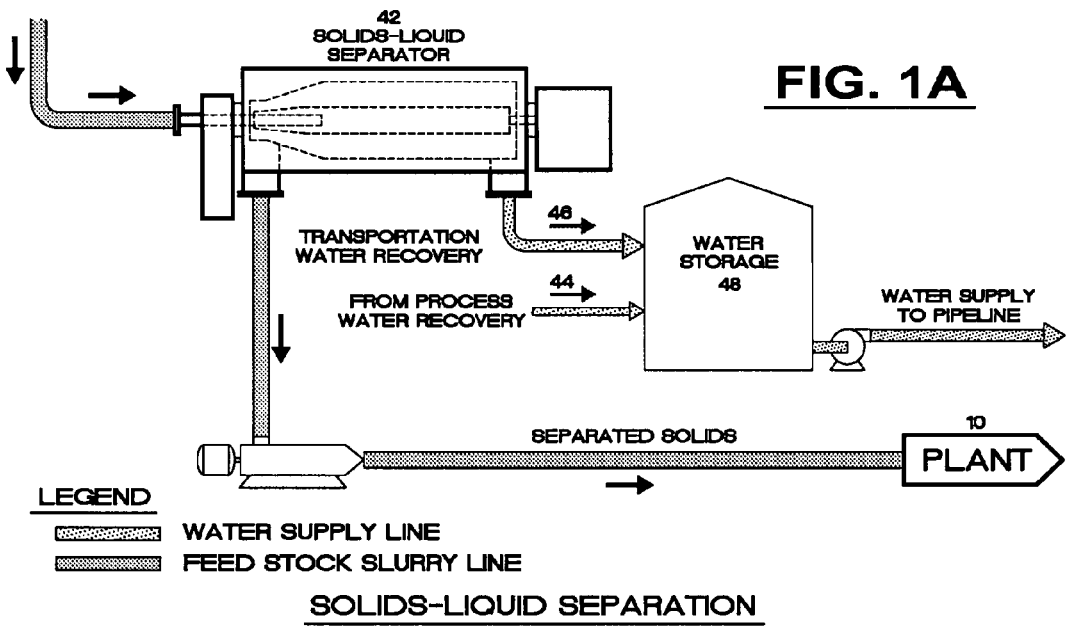
FIG. 1A is a detail of FIG. 1, depicting a typical water removal system using a centrifuge. Alternatively, a cane press, screw presses or the like water removal apparatus may be used.
Figure 1B:
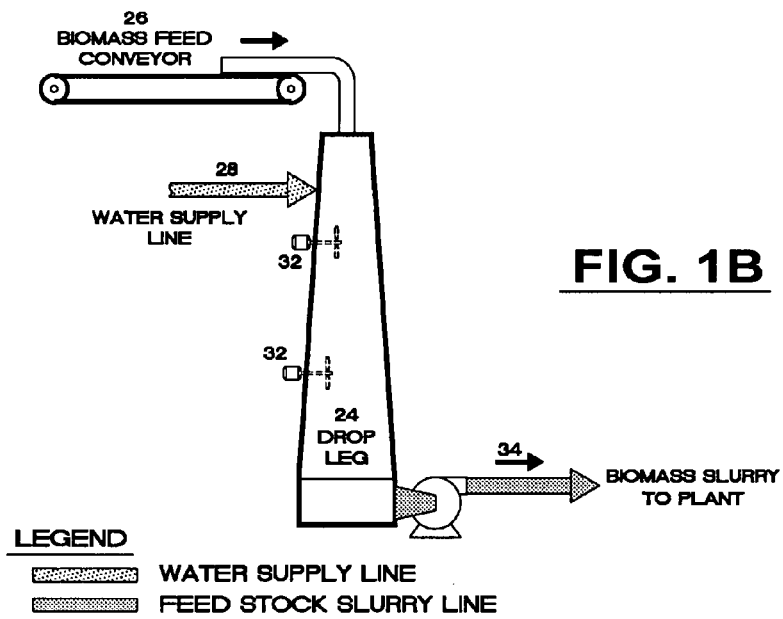
FIG. 1B is a detail of FIG. 1, depicting the details of a dropleg system to introduce solids into the pipeline to form a slurry. Alternative solids introduction apparatus may also be used.

After delivery, the biomass is introduced into the slurry at the collection points 20, for example using a dropleg 24, so that a slurry is formed with the circulating water, as shown in FIG. 1B. In FIG. 1B, biomass is introduced to dropleg 24 by conveyor 26, water is supplied through supply line 28 and the slurry is agitated by stirrers 32. The slurry is pumped with a booster pump at 34 into the conduit network. The embodiment described is for illustration only. It is not necessary to use a dropleg. Alternative means, such as a star valve, extrusion screw feeder or the like conventional solids handling means may also be used.

The biomass is chopped beforehand, or at the collection point, preferably to a range of ½ inch to ½ inch. A cane press or disk refiner may be used to fractionate the biomass so that it can be more easily contacted with the acid or alkali for pH adjustment. A cane press is probably more suited for grasses or straws while the disk refiner might be more applicable for wood chips.

The slurry is then transported to the next collection point by pumps provided at each collection point or at lift stations as required. The amount of water in the slurry may be determined by one of ordinary skill in the art, depending on the pump capacity, pipe size, etc., however, it is contemplated that a slurry having a solids content of about 5 wt % is sufficiently transportable through the network of pipes. A standpipe, with a large diameter relative to the pipes in the network of pipes, may be used to accommodate pressure variations in the network, or the standpipe may be used in conjunction with a dropleg, star valve or extrusion screw feeder to input solids into the network.

As shown in FIG. 4 and FIG. 5, it may be desirable to combine the streams entering and leaving the plant into larger diameter pipes 70 for transport to the centrally located refining plant to reduce the overall length of the pipe. In that context, it may be necessary to split the water stream coming from the refining plant or at later collection points to maintain the water balance. In this context, "splitting" means dividing a single larger stream into a plurality of smaller streams. The figures depict joining streams of slurry transported from two or more of the plurality of collection points into a single slurry stream directed to the refining plant and splitting the water removed from the slurry coming from the refining plant for recirculation.

Another important aspect of the system is that water, once charged into the network, including excess recovered process water, is reused for transport and the amount of water in the system remains relatively constant, generally without requiring make-up water. Because biomass contains in a range of about 12 percent to about 50 percent moisture, the addition of biomass to the system results in an increase in the amount of circulating water in the system. A part of this water may be used up in the refining process, for example as steam, or water may be treated and discharged, as necessary to maintain a constant amount of water in the network. In this context, a relatively constant amount of water will have the meaning ascribed to that term by one of ordinary skill in the art. Preferably, a relatively constant amount of water is an amount required to maintain a solids/liquids ratio of less than 15%.

Typically, the amount of water in the system will not vary over the course of operation more than ±5 percent.

The network of conduits is arranged so that the refining plant is accessible from all of the collection points via a continuous path which carries the slurry of biomass and water to the centrally located refining plant. In FIG. 1, the generalized loop diagram illustrates the conduits coming into the plant with feedstock, the water being recovered and fed back into the pipeline for transporting additional feedstock. In embodiments, the system is designed so that loops can be added to an existing network of conduits, as additional refining capacity is added, to bring the total production to the scale of a small oil refinery processing 90,000 to 100,000 barrels. These numbers are for illustration purposes only and are not to be considered limiting to the invention.

It is preferred that the conduit loops are sized so that 1000 tons/day or more can be collected from collection points in a single loop. A system may be provided with a plurality of conduit loops which can be operated independently, so that one or more loops can be removed from the system, from time to time. In the same manner additional loops can be added in the event more plant capacity and/or agricultural area is added.

The size of the pipes may be determined by one of ordinary skill in the art. For example, in the system shown in FIG. 3, based on a system adapted to accumulate approximately 12,500 tons per day, pipes having a diameter of approximately 24 inches could be effectively used, transporting slurry at approximately 5 ft/sec.

FIG. 2 depicts a loop system of three loops, a loop being defined as a continuous conduit system with each loop passing through the refiner and at least two collection points. A system of loops is a plurality of such loops.

Water is removed from the slurry at the refining plant using a cane press or other slurry water removal means known in the art, including without limitation, centrifugal apparatus, extruders, screens or filters. The water is thereafter recirculated in the network. In an embodiment depicted in FIG. 1A, solids-liquid separation is conducted in a solids-liquid separator such as centrifuge 42. Separated solids are directed to refining plant 10. Water recovered from the refining process 44 and water removed from the slurry 46 may be stored in water storage 48 which may then be used to supply water to the conduit network.

As noted above, the particular biomass refining technology used is not critical to the operation of the collection system. A plant as described in the aforesaid U.S. Pat. Nos. 4,461,648 and 5,916,780 may be used. As noted therein, preconditioning followed by pretreatment is typically required to initially break the bonds between the lignin and cellulose. Thus, in the practice of this invention, acidic or basic circulating water can optionally be used so that preconditioning is effected in the circulating system. For an acid solution, a 2% sulfuric acid solution may be suitable for this purpose, with the exact requirements being determined based on the skill of one of ordinary skill in the art based on the feedstock and refining process being used.

The foregoing description of the preferred embodiments is for illustration only and is not to be deemed limiting of the invention, which is defined in the appended claims.

What is claimed is:

1. A biomass collection and refining system for delivering ligno-cellulosic feedstock to a biomass refining plant for conversion into a fuel comprising:
   a) a plurality of collection points, each including a system for introducing chopped ligno-cellulosic feedstock into a circulating water stream to form a water-ligno-cellulosic feedstock slurry;
   b) a conduit loop, connected to the plurality of collection points, for carrying the circulating water stream, wherein the plurality of collection points are arranged in series along the conduit loop;
   c) a water removal system connected to the conduit loop for:
      i. receiving from the conduit loop the water-ligno-cellulosic feedstock slurry;
      ii. separating the ligno-cellulosic feedstock in the water-lignocellulosic feedstock slurry from the water;
      iii. delivering the ligno-cellulosic feedstock to a biomass refining plant; and
      iv. reintroducing separated water into the conduit loop; and
   d) a biomass refining plant for receiving the ligno-cellulosic feedstock from the water removal system and converting the ligno-cellulosic feedstock into a fuel.

2. The system according to claim 1, comprising a plurality of conduit loops connecting the collection points.

3. The system according to claim 2, wherein the system is adapted for collection of at least about 1,000 tons of ligno-cellulosic feedstock per day per loop.

4. The system according to claim 2, wherein the system is adapted for collecting in excess of about 50,000 tons per day of ligno-cellulosic feedstock.

5. The system according to claim 1, having a plurality of collection points for the collection of about 1,000 tons per day to about 50,000 tons per day of ligno-cellulosic feedstock.

6. The system according to claim 1, having between about 7 and 100 collection points.

7. The system according to claim 1, wherein water or slurry streams carried from two collection points are combined and transported to the refining plant, and water removed from the slurry at the refining plant is split for recirculation.

8. The system according to claim 1, wherein the amount of water in the system is relatively constant.

9. The system according to claim 1, wherein the system maintains the solids to liquids ratio in the slurry equal to or less than 15% by weight.

10. The system according to claim 1, wherein the water removal system comprises a cane press, extruder, centrifuge, screen, filter, screw presses or combination thereof.

* * * * *